(12) United States Patent
Kimble

(10) Patent No.: US 8,221,603 B2
(45) Date of Patent: Jul. 17, 2012

(54) MEMBRANE TRANSDUCER SURFACE CONTACT SENSOR

(75) Inventor: Michael C. Kimble, Westford, MA (US)

(73) Assignee: Reactive Innovations, LLC, Westford, MA (US)

( * ) Notice: Subject to any disclaimer, the term of this patent is extended or adjusted under 35 U.S.C. 154(b) by 477 days.

(21) Appl. No.: 12/492,431

(22) Filed: Jun. 26, 2009

(65) Prior Publication Data

US 2009/0321280 A1 Dec. 31, 2009

Related U.S. Application Data

(60) Provisional application No. 61/133,311, filed on Jun. 27, 2008.

(51) Int. Cl.
*G01N 27/26* (2006.01)
*G01N 17/00* (2006.01)
*G01F 1/64* (2006.01)

(52) U.S. Cl. ............... 204/416; 205/790.5; 204/415; 204/404

(58) Field of Classification Search ............... 205/790.5; 73/718; 204/403.06, 404, 416
See application file for complete search history.

(56) References Cited

U.S. PATENT DOCUMENTS

| 5,016,201 | A | * | 5/1991 | Bryan et al. | 700/267 |
| 6,151,969 | A | * | 11/2000 | Miller et al. | 73/808 |
| 6,365,034 | B1 | * | 4/2002 | Spellane | 205/775.5 |
| 6,805,788 | B1 | * | 10/2004 | Gonzalez-Martin et al. | 205/775.5 |
| 7,086,288 | B2 | | 8/2006 | Lee et al. | |
| 2007/0144919 | A1 | * | 6/2007 | Cheng | 205/789 |

OTHER PUBLICATIONS

G. Schiavon, G. Zotti. "Amperometric Monitoring of Sulphur Dioxide in Liquid and Air Sampled of Low Concductivity by Electrodes Supported on Ion-exchange Membranes," Analyst, vol. 116, pp. 797-801, Aug. 1991.*
Buchmann, Isidor. "Advances in Battery Rapid-Testing." Batteries Digest. Downloaded Aug. 13, 2009. <http://www.batteriesdigest.com/electrochemical_impedance_spectroscopy.htm>.
"Cyclic voltammetry." Wikipedia, The Free Encyclopedia. May 20, 2009, 18:39 UTC. <http://en.wikipedia.org/w/index.php?title=Cyclic_voltammetry&oldid=291229452>.
"Electrochemical impedance spectroscopy." Wikipedia, The Free Encyclopedia. Jul. 8, 2009, 22:16 UTC. <http://en.wikipedia.org/w/index.php?title=Electrochemical_impedance_spectroscopy&oldid=301076355>.
"Electrochemical potential." Wikipedia, The Free Encyclopedia. Aug. 7, 2009, 20:25 UTC. <http://en.wikipedia.org/w/index.php?title=Electrochemical_potential&oldid=306663577>.
"Nafion." Wikipedia, The Free Encyclopedia. Jun. 4, 2009, 13:41 UTC. <http://en.wikipedia.org/w/index.php?title—Nafion&oldid=294374874>.

(Continued)

*Primary Examiner* — Jeffrey T Barton
*Assistant Examiner* — Louis Rufo
(74) *Attorney, Agent, or Firm* — Hamilton, Brook, Smith & Reynolds, P.C.

(57) ABSTRACT

A surface-contact sensor includes a housing defining an opening, an ion-permeable membrane at the opening, a counterelectrode within the housing, and a reference electrode within the housing that is spaced apart from the current-collector. A current-collector pad includes a grommet support having a base and a lumen defining an opening. An ion-permeable membrane spans at least a portion of the opening of the grommet. The ion-permeable membrane is held in place by a gasket surrounding the lumen. A current collector, at least in one embodiment, is proximate to a portion of the ion-permeable membrane that spans the opening.

17 Claims, 3 Drawing Sheets

OTHER PUBLICATIONS

"Reference electrode." *Wikipedia, The Free Encyclopedia.* Jul. 14, 2009, 11:15 UTC. <http://en.wikipedia.org/w/index.php?title=Reference_electrode&oldid=302026623>.

"Nafion—Perfluorosulfonate Ionomer." *The Mauritz Research Group.* Downloaded Aug. 13, 2009. <http://www.psrc.usm.edu/mauritz/nafion.html>.

* cited by examiner

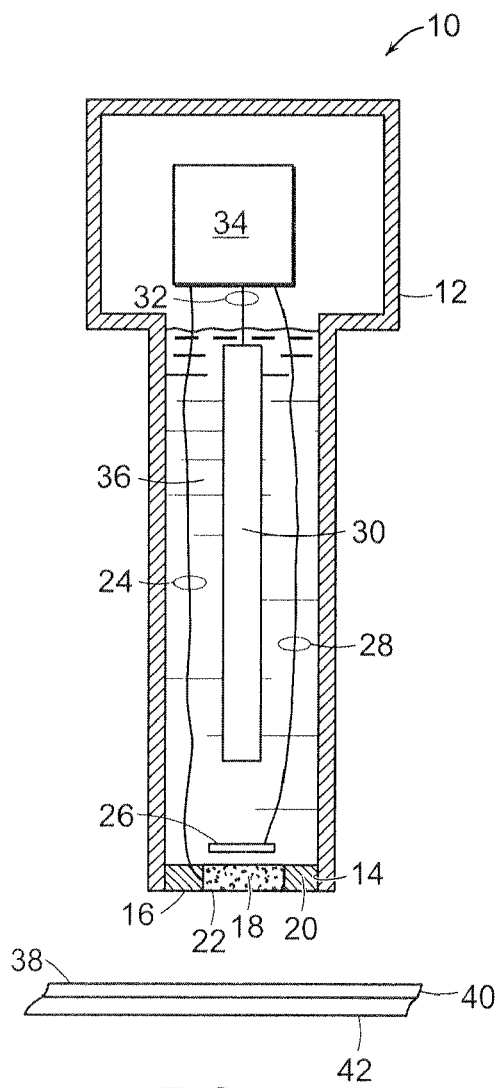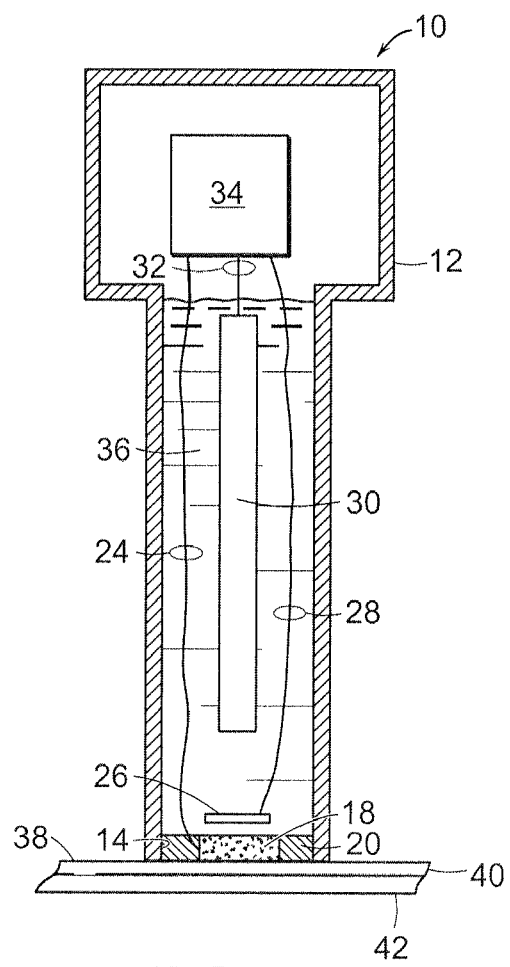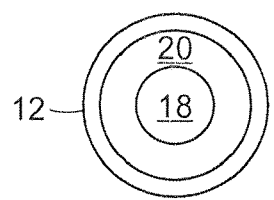
FIG. 1A FIG. 1B
FIG. 1C

MEMBRANE TRANSDUCER SURFACE CONTACT SENSOR

RELATED APPLICATION

This application claims the benefit of U.S. Provisional Application No. 61/133,311, filed on Jun. 27, 2008. The entire teachings of the above application are incorporated herein by reference.

BACKGROUND OF THE INVENTION

The condition of a surface can dictate the performance of many devices. For example, platinum films are often used to catalyze reactions. Other examples of reactive surfaces include biocatalytic coatings, fuel cell and battery electrodes, photocatalytic coatings, and industrial catalysts. Reduction in performance of the devices can be due to contamination, degradation of the surface, such as by corrosion, and by wear. Often materials employed to form reactive surfaces are extremely expensive and, at the same time, highly sensitive to environmental factors or even perishability over time.

Destructive testing, of course, can be employed to determine the condition of surfaces, but at the cost of compromising the integrity of the device employing the surface that is tested. As a quality control issue, if there is no other alternative, sampling of production lines will result in sacrifice of selected units for the purpose of maintaining a statistically high probability of acceptability in the remaining units. Statistical techniques, however, are never as good as testing each unit, and nondestructive testing is the only alternative. Further, nondestructive evaluation (NDE) is often employed to conduct inspection for defects that cannot be measured by destructive testing, such as identification of the size and location of surface and subsurface flaws and defects, such as cracks, voids and corrosion. Methods of NDE include, for example, visual inspection, liquid penetration inspection, acoustic emission monitoring, magnetic particle inspection, eddy current testing, ultrasonic inspection and radiographic inspection. However, NDE methods have their own limitations relative to destructive testing. A primary example of a common limitation of nondestructive testing is an inability to assess the propensity of a reactive surface to react as intended. Therefore, even with a combination of destructive and nondestructive techniques, testing of reactive surfaces remains limited, thereby capping the reliability of instrumentation and testing devices that employ reactive surfaces.

Therefore, a need exists for a device and method that overcomes and minimizes the above-referenced problems.

SUMMARY OF THE INVENTION

The present invention is directed to a device and method for nondestructive testing of reactive surfaces.

One embodiment of the invention is a surface-contact sensor that includes a housing defining an opening, an ion-permeable membrane at the opening, a counterelectrode within the housing, and a reference electrode within the housing. The reference electrode is spaced apart from the current collector.

In another embodiment, the invention is a current-collector pad. The current-collector pad includes a grommet support having a base and a lumen that defines an opening. An ion-permeable membrane spans at least a portion of the opening. The ion-permeable membrane is held between the lumen and a gasket that surrounds the lumen. A current-collector is located near a portion of the ion-permeable membrane that spans the opening.

In another embodiment, the invention is a method for characterizing a substrate surface. The method includes applying a working surface to a substrate surface. The working surface includes an ion-permeable membrane, wherein the ion-permeable membrane partitions the substrate surface from a counterelectrode and a reference electrode. Further, the reference electrode and the counterelectrode are in electrical communication with the ion-permeable membrane through an electrolyte. Current is collected from the substrate surface through the working surface to measure an electrochemical response by the substrate surface, thereby characterizing the substrate surface.

The present invention has many advantages. For example, the ion-permeable membrane of the surface-contact sensor and current-collector pad of the invention can be directly contacted with a reactive surface to be tested without damaging the surface. A current collector provides for collection of electrons from the reactive surface through the ion-permeable membrane, also without damaging the reactive surface. Employment of standard techniques, such as cyclic voltammetry, can then be employed to characterize the surface relative to a known standard. The result obtained is a measure of the propensity of the reactive surface to react as intended, and is obtained without damaging the surface. Other types of testing that can be conducted include electrochemical impedance spectroscopy (EIS) and reactive electrochemical impedance spectroscopy (REIS). In another embodiment, a power supply can be employed, along with a lead connected to the substrate. Application of a current through the substrate by use of the power supply can induce a chemical reaction in the substrate to enable further characterization of the surface by the techniques just described, such as cyclic voltammetry and EIS or REIS. The methods of the invention can be conducted by the surface-contact sensor and current-collector pad assembled into a portable unit, such as a handheld portable unit, that permits quick, accurate and comprehensive testing of reactive surfaces without the limitations of other nondestructive techniques and without requiring sampling and sacrifice of expensive units in a production line.

BRIEF DESCRIPTION OF THE DRAWINGS

FIGS. 1A, 1B and 1C are schematic representations of one embodiment of a surface-contact sensor of the invention.

DETAILED DESCRIPTION OF THE INVENTION

Figure 2:
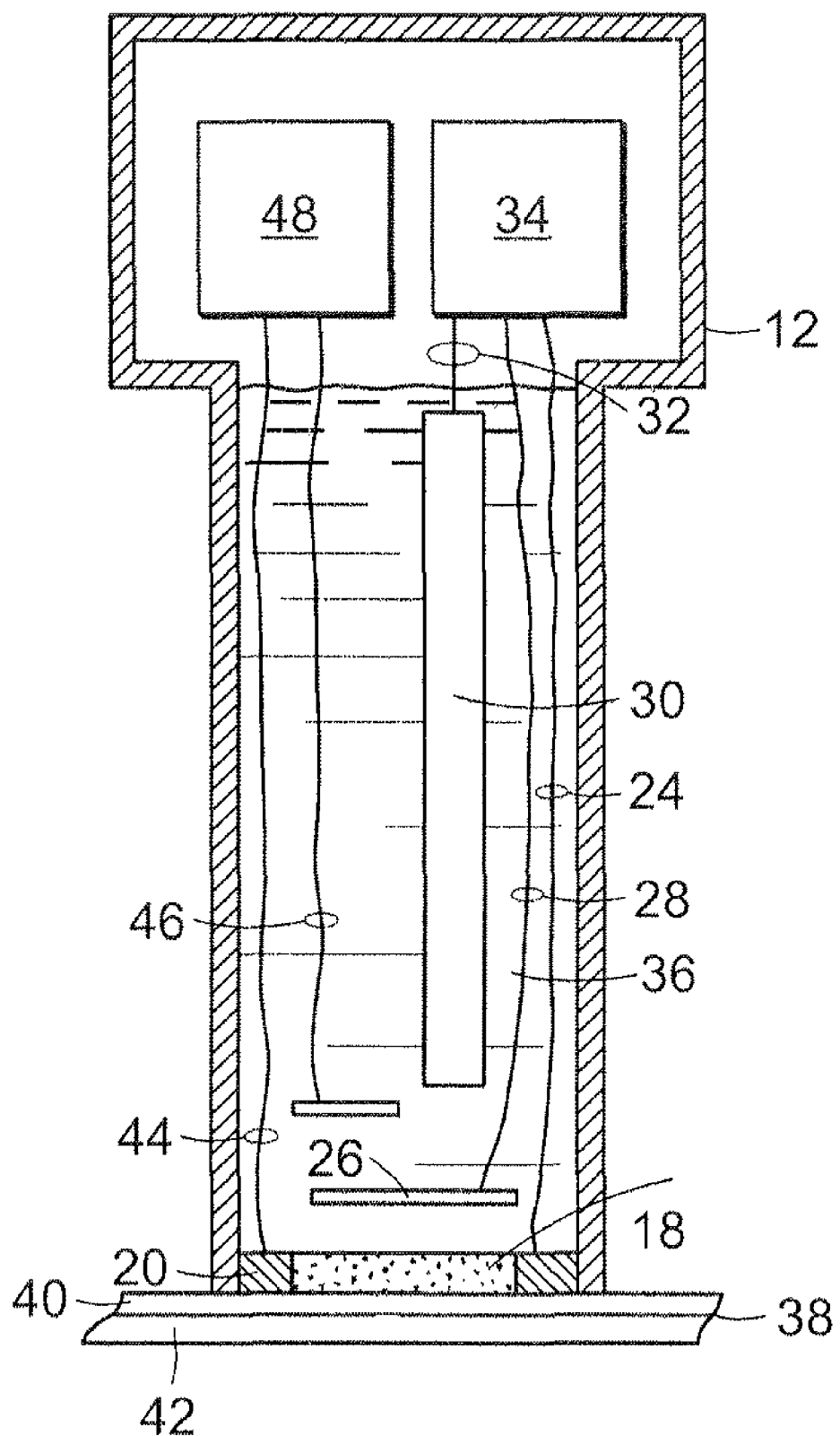
FIG. 2 is a schematic representation of another embodiment of a surface-contact sensor of the invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

Generally, the invention is directed to an apparatus and method for characterizing the condition of a reactive surface. The apparatus nor the method harm or in any way affect the quality of the reactive surface, thereby permitting comprehensive testing of analytical devices, such as during initial testing in a production run of devices or on site over time to ensure continued and consistent performance of devices during use. The apparatus of the invention can be portable, and the method practiced by use of the method can be preprogrammed into the device for convenience and rapid quality control.

In one embodiment, the apparatus is a surface-contact sensor represented schematically in FIGS. 1A, 1B and 1C. As shown therein, surface-contact sensor 10 includes housing 12 defining opening 14. Housing 12 can be constructed of any suitable material, such as any rigid thermoset or thermoplastic polymer. The housing can be configured as a handheld unit that contains any necessary portable power supply and circuitry necessary to conduct whatever tests are required of surface-contact sensor 10. Optionally, surface-contact sensor 10 can include a port (not shown) for uploading or downloading information to a portable central processing unit within surface-contact sensor 10. Examples of such information can include, for example, programming related to the type of testing to be conducted by surface-contact sensor 10, data collected by surface-contact sensor 10 and information related to calibration of surface-contact sensor 10, such as calibration information related to replacement parts of surface-contact sensor 10. Examples of replaceable components of surface-contact sensor 10 that may require calibration of the system include a reference electrode, an electrolyte or a membrane. Another example of a replaceable component of surface-contact sensor 10 may be a current-collector pad, discussed below.

Current-collector pad 16 is at opening 14 and, preferably seals opening 14. Current-collector pad includes ion-permeable membrane 18 extending at least partially across opening 14 and current collector 20. Ion-permeable membrane 18 can be of any suitable ion-permeable material known in the art. Examples of suitable ion-permeable membrane materials include Nafion®, Perfluorosulfonate Ionomer, commercially available from EI DuPont de Nemours & Company. Other suitable ion-permeable membranes include those used in fuel cell and electrochemical systems as is known in the art. The thickness of ion-permeable membrane typically is in a range of between about 0.05 and about 0.18 millimeters.

Current-collector 20 is proximate to ion-permeable membrane 18. Preferably, and as shown in FIG. 1C, current-collector extends about periphery of ion-permeable membrane. In an alternative embodiment, current-collector 20 is located about periphery of ion-permeable membrane 18, but not over any portion of a surface of ion-permeable membrane 18 that extends across coplanar surface 22.

Returning to FIG. 1A, ion-permeable membrane 18 and current-collector 20 present coplanar surface 22, which can be applied to a reactive surface work piece for testing of that work piece. Current-collector 20 can be, for example, a suitable metal deposited over at least a portion of ion-permeable membrane 18, such as about a periphery of ion-permeable membrane 18. In one embodiment, current-collector 20 is platinum that has been deposited by a suitable technique, such as chemical platinization, physical vapor deposition, or slurry coating. In embodiments where current-collector 20 extends completely across ion-permeable membrane 18, the thickness of current-collector 20 is sufficiently thin to permit movement of ions, such as hydrogen ions, across current-collector 20 and ion-permeable membrane 18. Preferably, current-collector 20 is of a material that is essentially inert to a reactive surface with which it is in contact or with any other materials with which it is in contact during use of surface-contact sensor 10. Examples of other suitable materials include gold, silver, noble metals and carbon.

Ion-permeable membrane 18 and current-collector 22 are supported by suitable means at opening 14, such as are described below. Wire lead 24 extends from current-collector 20 through housing. Wire lead 24 can extend from housing at a location remote from current-collector 20 or, alternatively, can be connected to a central processing unit located on board surface-contact sensor 10. Counterelectrode 26 is located within housing 12. Counterelectrode lead 28 extends from counterelectrode 26 through housing to either CPU unit 34 or extends from housing 12, at a location that is remote to counterelectrode 26 such as to a suitable commercial electroanalytical test apparatus. CPU 34 can include the circuitry for operating the sensor, including potentiostatic, galvanostatic, and electrochemical impedance spectroscopic methods, for example, which are located on board surface-contact sensor 10. Examples of suitable materials of construction of counterelectrode 26 include platinum and other noble metals. A high surface area counter electrode is employed that can be driven to high positive and negative potentials to impart the desired redox behavior at the working electrode. This counter electrode is contained in the wand. A platinum mesh disc with a diameter of approximately 0.25 inches can serve as the counter electrode that is subsequently electroplated with a chloroplatinic acid solution to increase the surface area.

Reference electrode 30 extends within housing 12. Examples of suitable materials for reference electrode 30 include platinum. The reference electrode is located within the hand-held sensor wand and is compatible with the membrane transducer and electrolyte. A silver chloride based reference electrode commonly used in cyclic voltammetry can be used by electrodepositing AgCl onto a silver wire. Typically, this AgCl coated silver wire is housed in a saturated silver chloride solution isolated from the main electrolyte (0.5 M $H_2SO_4$ for our case) via a salt bridge or porous frit. In order to obtain a long-life operating sensor probe, the use of the silver chloride solution in the reference electrode can be eliminated that would eventually leach through the salt bridge or porous glass frit and ion-exchange with the membrane transducer. Thus, the AgCl coated silver wire can be used directly in the sensor electrolyte such as a 0.5 M $H_2SO_4$. Furthermore, to help protect the reference electrode, it can be coated with a thin layer of Nafion ionomer to electrically isolate it from the counter electrode as well as to minimize contamination to the membrane transducer. Reference electrode lead 32 extends from reference electrode 30 to either CPU unit 34, located on board surface-contact sensor 10 or extending from housing 12 at a remote location.

Electrolyte 36 fills at least a portion of housing 12 and partitions ion-permeable membrane 18, counterelectrode 26 and reference electrode 30 from each other. Examples of suitable electrolytes include sulfuric acid with concentration ranges from 0.00001 M to 2.0 M. Other electrolytes include those that dissociate into a proton or those that dissociate into other cations including sodium and potassium.

FIG. 1B is an assembled view of surface-contact sensor 10 in contact with surface substrate 38 as a work piece, the reactive surface of which is to be tested by surface-contact sensor 10. Substrate surface 34 functions as a working electrode during operation of surface-contact sensor 10 and is electrically conducted. Typically, substrate surface 34 includes working electrode component 40 and working electrode substrate 42 that supports working electrode 40. Examples of substrate surfaces suitable for testing by surface-contact sensor 10 are those that will release an ion upon application of surface-contact sensor 10 to substrate surface 38 in an application of sufficient voltage and current to conduct surface testing of substrate surface 38 by any known electroanalytical interrogation methodology known, such as cyclic voltammetry or electrochemical impedance spectroscopy.

In an alternative embodiment, represented in FIG. 2, surface-contact sensor 10 includes negative electrical lead 44 at planar working surface 22 and positive lead 42 immersed in electrolyte 34 within housing 12. Negative lead 44 and positive lead 46 connect to power supply 48 by application of electrical potential between negative lead 44 and positive lead 46, reaction can be induced at substrate surface 34 during characterization of substrate surface 34 by the electroanalytical interrogation methodologies described above. In still another embodiment (not shown), negative lead 44 can be connected to substrate surface 34, such as working electrode 36 or working electrode substrate 38 at a location remote from surface-contact sensor 10. In still another embodiment, the electrical leads can be reversed so that lead 44 is the positive lead and lead 46 is the negative lead that connect to power supply 48.

A current-collector pad of the invention includes, in one embodiment, a grommet support having a base and a lumen defining an opening that is formed of an insulating material, such as a plastic or polymer. An ion-permeable membrane spans at least a portion of the opening defined by the grommet support. The ion-permeable membrane is held between a gasket of the current-collector pad and the lumen. A current-collector is proximate to the portion of the ion-permeable membrane that spans the opening. All of the embodiments of the current-collector of the invention can be adapted to be disposable or replaceable.

Figure 3:
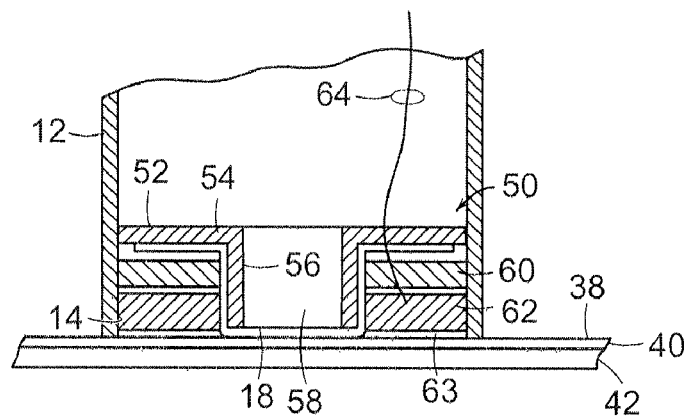
FIG. 3 is a cross-sectional view of one embodiment of a current-collector pad of the invention.

In one embodiment, shown in FIG. 3, current-collector pad 50 is located at opening 14 of housing 12 of a surface-contact sensor of the invention. Current-collector pad 50 can be disposable or replaceable. Current-collector pad 50 includes grommet 52 having base 54 and lumen 56 extending from base 54. Lumen 56 defines opening 58. Ion-permeable membrane 18 spans opening 58 and covers at least a substantial portion of one side of lumen 56 and base 54. Gasket 60 extends about the periphery of lumen 56 and holds ion-permeable membrane 18 between gasket 60 and grommet 52 at lumen 56 and base 54, thereby maintaining tension of ion-permeable membrane 18 at opening 58. Metal washer 62 extends about periphery lumen 56 and can be held in place by, for example, an interference fit with ion-permeable membrane 18 and lumen 56. Side 63 of metal washer 62 and the portion of ion-permeable membrane 18 spanning opening 58 define a substantially continuous working surface. Preferably, the substantially continuous working surface is essentially planar. Metal washer 62 is connected to an electrical lead 64 extending from metal washer through housing 12. Examples of suitable materials of metal washer 62 include, for example, stainless steel, noble metals, and noble metal coated washers such as a platinum coated steel washer. Where metal washer 62 is formed of a material that itself may be susceptible to reaction, or contamination of a reactive surface, preferred uses of such embodiments of current-collector pad 50 include, for example, corrosion testing, or other embodiments where contamination or minor reaction of the current-collector will not significantly affect a test result.

Figure 4:
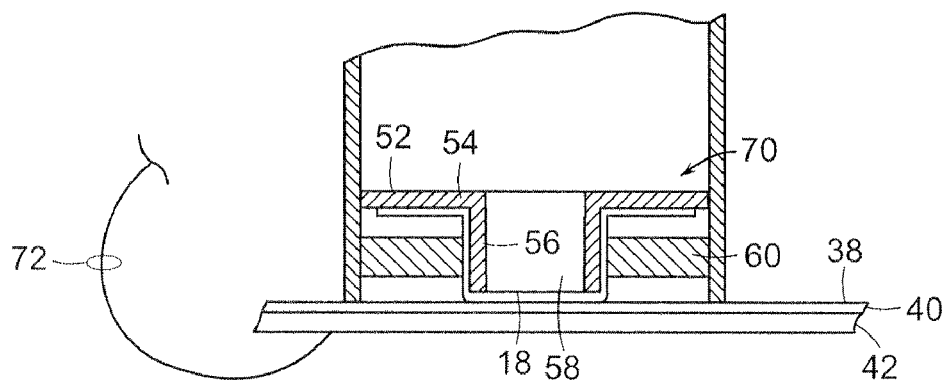
FIG. 4 is a cross-sectional view of another embodiment of a current-collector pad of the invention.

In another embodiment of the invention, current-collector pad 70, shown in FIG. 4, includes grommet 52, having base 54 and lumen 56. Ion-permeable membrane 18 is held in place by gasket 60. In this embodiment, there is no metal washer 62. Instead, electrical lead 72 extends from a conductive working electrode substrate 42 that underlies a reactive surface 40 that is being tested. Typically, in such embodiments, the reactive surface 40 is nonconductive. Embodiments of current-collector pads of the invention, such as are represented in FIG. 4, typically are employed to test surfaces that are employed as insulative coatings, or which are porous.

Figure 5:
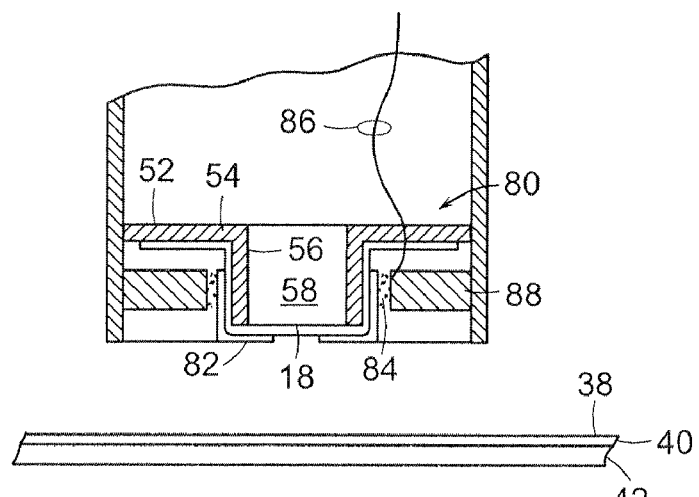
FIG. 5 is a cross-sectional view of still another embodiment of a current-collector pad of the invention.

In another embodiment, shown in FIG. 5, current-collector 80 includes grommet 52, over at which a portion of which ion-permeable membrane 18 is overlaid. At least a portion of ion-permeable membrane 18 spanning opening 58 is platinized by a suitable technique, such as chemical platinization, physical vapor deposition and variations thereof, and slurry coating. Platinization 82 also extends along at least a portion of ion-permeable membrane surrounding perimeter of lumen 56. Wire 84 is wrapped about lumen 56 at platinized surface 82 and is in electrical contact with platinized surface 82. Examples of suitable wire material include platinum, copper, cladded wires, and noble metal clad or continuous wires. Electrical lead 86 extends from wire 84 to a CPU or other appropriate instrument (not shown) as appropriate. Insulating gasket 86 extending about ion-permeable membrane 18 at lumen 56 and wire 84 holds both in place. Suitable materials of gasket 88 include silicone, plastic, epoxies and adhesives.

The invention is further described by the following examples which are not intended to be limiting.

Equivalents

While this invention has been particularly shown and described with reference to preferred embodiments thereof, it will be understood by those skilled in the art that various changes in form and details may be made therein without departing from the scope of the invention as encompassed by the appended claims.

What is claimed is:

1. A surface-contact sensor, comprising:
a) a housing having an end and defining an opening at the end;
b) an ion-permeable membrane at the opening;
c) a current collector linked to the housing that is proximate to the ion-permeable membrane, wherein the current collector and the ion-permeable membrane collectively form a substantially planar continuous working surface at the end of the housing and wherein the current collector extends about a perimeter of the ion-permeable membrane, whereby the ion-permeable membrane and the current collector can simultaneously contact a planar surface;
d) a counter electrode within the housing; and
e) a reference electrode within the housing and spaced apart from the current collector.

2. The surface-contact sensor of claim 1, wherein the current collector covers the ion-permeable membrane at the working surface.

3. The surface-contact sensor of claim 1, wherein the current collector includes a metal at the working surface that is at least one member selected from the group consisting of platinum, gold and carbon.

4. The surface-contact sensor of claim 3, wherein the current collector includes platinum.

5. The surface-contact sensor of claim 4, wherein current collector includes a layer of platinum at the working surface.

6. The surface-contact sensor of claim 5, wherein the layer of platinum extends about the perimeter of the ion-permeable membrane.

7. The surface-contact sensor of claim 1, wherein the ion-permeable membrane includes at least one member selected from the group consisting of ion-containing polymers, ion-transfer porous media, and micro-porous media.

8. The surface-contact sensor of claim 7, wherein the ion-permeable membrane includes an ion-containing polymer.

9. The surface-contact sensor of claim 8, wherein the ion-containing polymer includes a tetrafluoroethylene polymer.

10. The surface-contact sensor of claim 9, wherein the tetrafluoroethylene polymer is a sulfonated tetrafluoroethylene copolymer.

11. The surface-contact sensor of claim 10, wherein the sulfonated tetrafluoroethylene copolymer has a thickness in a range of between about 0.05 mm and about 0.18 mm.

12. The surface-contact sensor of claim 1, further including a first electrical lead at the working surface and a second electrical lead within the housing, whereby application of an electrical potential across the first and second leads will divert an electrical current across at least a portion of the working surface when the surface contact sensor contains an electrolyte between the first and second electrical leads, and when the working surface is in contact with the electrically conductive substrate surface.

13. The surface-contact sensor of claim 1, wherein the housing is elongate, and the working surface is at one end of the housing.

14. The surface-contact sensor of claim 13, further including a power supply electrically connected to the ion-permeable membrane, the contact electrode and the reference electrode.

15. The surface-contact sensor of claim 14, further including electrical circuitry that conducts an electroanalytical interrogation in combination with the working surface.

16. The surface-contact sensor of claim 15, wherein the electroanalytical interrogation is at least one member selected from the group consisting of cyclic voltammetry, electrical impedance spectroscopy, and reactive electrochemical impedance spectroscopy.

17. The surface-contact sensor of claim 16, wherein the sensor is self-contained.

* * * * *